United States Patent [19]

Faith et al.

[11] Patent Number: 4,806,535

[45] Date of Patent: Feb. 21, 1989

[54] IMIDAZOLYLPHENYL AND 1,2,4-TRIAZOLYLPHENYL BENZOPYRIDAZINONE AND PYRIDOPYRIDAZINONE COMPOUNDS AND THEIR USE FOR INCREASING CARDIATONIC CONTRACTILITY

[75] Inventors: William C. Faith, Ambler; Henry F. Campbell, Lansdale; Donald E. Kuhla, Doylestown; William L. Studt, Harleysville; James L. Barnes, Glenside, all of Pa.

[73] Assignee: Rorer Pharmaceutical Corporation, Fort Washington, Pa.

[21] Appl. No.: 76,461

[22] Filed: Jul. 22, 1987

[51] Int. Cl.$^4$ ............ C07D 401/14; C07D 403/10; A61K 31/50
[52] U.S. Cl. .................. 514/248; 514/252; 544/236; 544/237; 546/315; 546/322; 546/116; 546/278; 548/341
[58] Field of Search ............ 514/248, 252; 544/236, 544/237

[56] References Cited

U.S. PATENT DOCUMENTS

| | | | |
|---|---|---|---|
| 4,289,774 | 9/1981 | Schracht et al. | 544/237 |
| 4,710,496 | 12/1987 | Geiss et al. | 514/248 |
| 4,734,415 | 3/1988 | Sircar et al. | 514/252 |

FOREIGN PATENT DOCUMENTS 0145019 6/1985 European Pat. Off. ............ 514/252

*Primary Examiner*—Donald G. Daus
*Assistant Examiner*—E. Bernhardt
*Attorney, Agent, or Firm*—Imre (Jim) Balogh; Martin F. Savitzky; James A. Nicholson

[57] ABSTRACT

This invention relates to imidazolylphenyl and 1,2,4-triazolylphenyl benzopyridazinone and pyridopyridazinone compounds of the formula

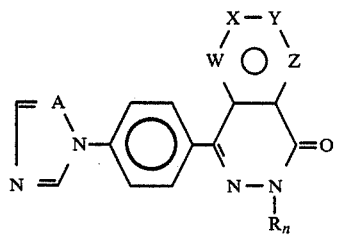

wherein A is CH or N and not more than one of W, X, Y and Z is a N atom which possess valuable pharmaceutical preparations, e.g., increasing cardiotonic contractility. Uses of said compounds including methods for increasing cardiac contractility and in the treatment of congestive heart failure, pharmaceutical compositions including the same and methods for the preparation thereof.

13 Claims, No Drawings

IMIDAZOLYLPHENYL AND 1,2,4-TRIAZOLYLPHENYL BENZOPYRIDAZINONE AND PYRIDOPYRIDAZINONE COMPOUNDS AND THEIR USE FOR INCREASING CARDIATONIC CONTRACTILITY

FIELD OF INVENTION

This invention relates to benzo and pyrido pyridazinone compounds useful as cardiotonic agents for the treatment of congestive heart failure, to their preparation and to pharmaceutical compositions including the same.

REPORTED DEVELOPMENTS

Congestive heart failure is a life threatening condition in which myocardial contractility is depressed such that the heart is unable to adequately pump the blood returning to it. Normal pathologic sequelae include decreased cardiac output, venous pooling, increased venous pressure, edema, increased heart size, increased myocardial wall tension, and eventually cessation of contractility. Digitalis glycosides have long been used to increase myocardial contractility and reverse the detrimental changes seen in congestive heart failure. More recently, dopamine, dobutamine, and amrinone have been used to provide necessary inotropic support for the failing heart.

Other reported inotropic drugs include the substituted pyridazinines disclosed in U.S. Pat. No. 4,353,905, wherein the 6-position of the pyridazinone is substituted by 4-imidazolyl phenyl, and in U.S. Pat. Nos. 4,397,854 and 4,404,203, where the 6-position of the pyridazinone is substituted by various substituted phenyl groups.

The present invention relates to a class of novel benzo and pyrido pyridazinone compounds which exhibit cardiotonic activity in humans and mammals.

SUMMARY OF INVENTION

This invention relates to the compounds described by the Formula I

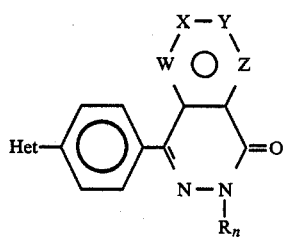

wherein:
Het is imidazol-1-yl or 1,2,4-triazol-1-yl;
W, X, Y and Z are C or not more than one is a N atom,
$R_n$ is hydrogen,
 alkyl,
 aralkyl,
 acyl,
 carbalkoxy,
 carbamyl,
 carbalkoxyalkyl,
 hydroxyalkyl,
 alkoxyalkyl or
 amidino; or a phamaceutically acceptable salt thereof.

This invention also relates to pharmaceutical compositions for use in increasing cardiac contractility in humans and to the uses of these compounds in the treatment of congestive heart failure in humans and other mammals.

DETAILED DESCRIPTION

The compounds of this invention which have particular usefulness as cardiotonic agents are described by Formula II below.

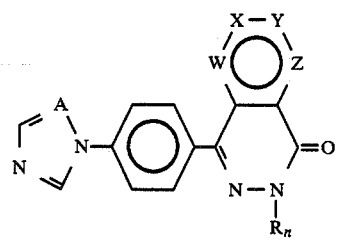

wherein W, X, Y, Z and $R_n$ are as described above and A is CH or N.

As employed above and throughout the disclosure, the following terms, unless otherwise indicated, shall be understood to have the following meanings.

"Alkyl" means a saturated aliphatic chain, either branched or straight, including up to about 6 carbon atoms.

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"Aralkyl" means an alkyl group substituted by an aryl radical. The preferred aralkyl groups are benzyl or phenethyl.

"Acyl" means an organic radical derived from an organic acid by the removal of its hydroxyl group. Preferred acyl groups are acetyl, propionyl, benzoyl, etc.

"Alkoxy" refers to a loweralkyl—O— group.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Compounds within the scope of Formula I may be prepared in accordance with one or more of the following reaction sequences.

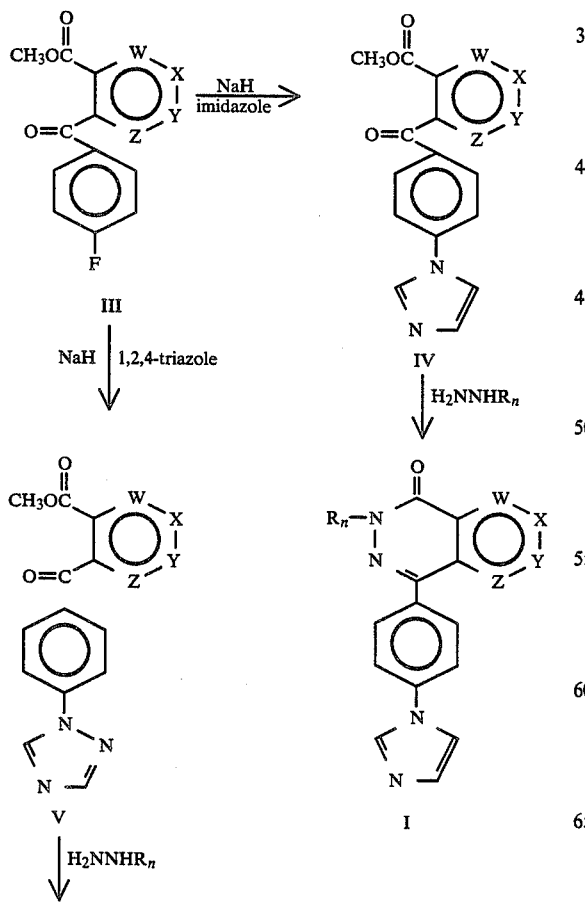

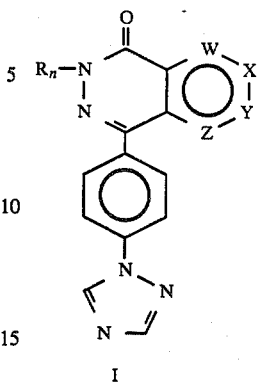

Treatment of the (4-fluorobenzoyl)benzoate or (4-fluorbenzoyl)pyridine carboxylate of formula III with sodium hydride and imidazole in DMF followed by heating to effect reaction results in the displacement of the fluorine and addition of the imidazole ring IV. The resultant 4-(1H-imidazol-1-yl)benzoyl benzoate and 4-(1H-imidazol-1-yl)benzoyl pyridine carboxylate addition products are then reacted with a hydrazine to form the cyclized end product of Formula I.

In a similar manner treatment of the (4-fluorobenzoyl)benzoate or (4-fluorbenzoyl)pyridine carboxylate of formula III with 1,2,4-triazole in place of imidazole results in the corresponding compounds of Formula V. This may then be treated with a hydrazine to obtain the cyclized triazole products of Formula I.

The starting materials are either known or can be prepared by the following reactions.

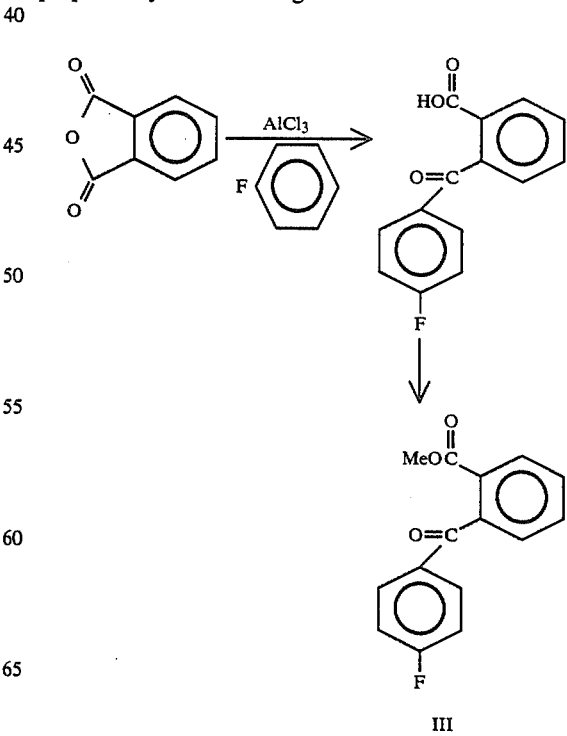

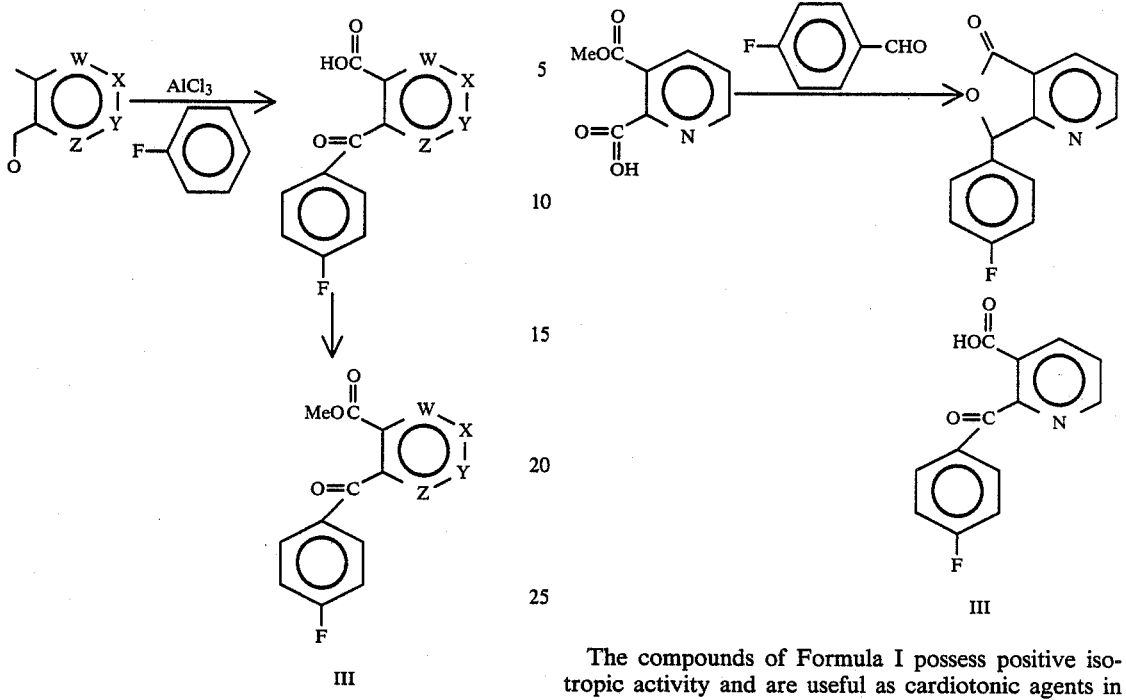

where one of W, X, Y and Z is nitrogen.

The 4-flurobenzoylbenzoate can be prepared by Friedel-Crafts reaction of phthalic anhydride with fluorobenzene in the presence of aluminum chloride or other Lewis acid. The product is isolated as an insoluble copper chelate. The resultant 2-(4-fluorobenzoyl)benzoic acid is then esterified with diazomethane.

The corresponding:

3-(4-fluorobenzoyl)pyridine-2-carboxylic acid;

4-(4-fluorobenzoyl)pyridine-3-carboxylic acid; and 3-(4-fluorobenzoyl)pyridine-4-carboxylic acid compounds may similarly be prepared from the 2,3-pyridine dicarboxylic anhydride or 3,4-pyridinedicarboxylic anhydride. The isomers are separable as a result of their dissimilar solubilities. Treatment with diazomethane results in the desired methyl ester product.

2-(4-Fluorobenzoyl)pyridine-3-carboxylate may be prepared using an alternate procedure utilizing a Hammick reaction. Thermal decomposition of 3-carbomethoxypicolinic acid in the presence of excess 4-fluorobenzaldehyde generates a lactone. Hydrolysis with dilute sodium hydroxide followed by dissolution and treatment with excess chromium oxide pyridine complex yields the starting material of Formula III. This is seen by the following reaction sequence.

The compounds of Formula I possess positive isotropic activity and are useful as cardiotonic agents in the treatment of humans and other animals, particularly other mammals for cardiac disorders including congestive heart failure. These compounds selectively inhibit the low Km cAMP-phosphodiesterase (Peak III) from dog heart and this may be a principal component of their mechanism of action. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

GANGLIONIC-BETA BLOCKED ANESTHETIZED DOG PROCEDURE

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncannulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37±1° C.

Following a 30 min. postsurgical stabilization period, control values are recorded. Myocardial depression is induced by ganglionic and beta receptor blockade. Initially, the responsiveness of the autonomic nervous system is assessed by performing a 30 sec. bilateral carotid occlusion (BCO). Ten minutes later, a saline solution of isoproterenol 0.3 mcg/kg i.v. is administered to assess beta receptor integrity. Ten minutes after that, a saline solution of mecamylamine 2 mg/kg i.v. is infused, followed by a saline solution of propranolol 1 mg/kg i.v. plus 0.3 mg/kg/hr. Twenty five minutes later, a second BCO is performed to demonstrate ganglionic blockade followed by a second injection of saline isoproterenol 0.3 mcg/kg i.v. to demonstrate beta blockade. Ten minutes later, the test compound or vehicle is administered intravenously in ascending doses at 30 min. intervals at 1.5 ml/ml in a total volume of 3.5 ml. On completion of the experiment, both BCO and isoproterenol challenges are repeated to verify ganglionic and beta blockade.

The results of the blocked dog test show that compounds of the present invention increase contractile force and aortic blood flow in a dose-related manner while maintaining arterial pressure and having minimal effects on heart rate.

Additional test procedures which have been found to be an efficient means for ascertaining the inotropic activity of the compounds of this invention are described below.

The following test procedure is a standard test for determining the oral activity of the present compounds.

CONSCIOUS INSTRUMENTED DOG

Mongrel dogs (10–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular end diastolic pressure, left ventricular $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

PIG ATRIA INOTROPIC SCREENING AT LOW CALCIUM CONCENTRATIONS

Guinea pigs are stunned by a sudden blow to the head; their chests are opened and hearts excised and placed in Kreb's medium (concentrations, mM:NaCl, 118:39; KCl, 4.70; $MgSO_4$, 1:18; $KH_2PO_4$, 1:18; $NaHCO_3$; 25.00; glucose, 11.66; and $CaCl_2$, 1.25) gassed with a mixture of 95% $O_2$5% $CO_2$. Left atria are removed and inserted into warmed 33° C. double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 20 gauge silver wire wound into a tight coil approximately 12–14 mm in diameter. Electrodes are connected to a Grass stimulator via Grass constant current unit. Tissues are driven at 90 pulses per minute with a 5 msec. duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentrations-response curves. Slopes for these regressions are calculated via the method of Finney (1971) and compared using Student's t-test.

The following in vitro method is another means for measuring the inotropic potency of the present compounds. This method is a modification of the enzyme inhibition method reported by Thompson, W. J. and Appleman, M. M., "Characterization of Cyclic Nucleotide Phosphodiesterase of Rat Tissue," J. Biological Chemistry, Vol. 246, pp. 3145–3150 (1971); and Thompson, W. J., Brooker, G. and Appleman, M. M., "Assay of Cyclic Nucleotide Phosphodiesterase with Radioactive Substrates," Methods in Enzymology, Vol. 38, pp. 205–212 (1974); and is believed to correlate to in vivo inotropic activity in humans.

INHIBITION OF PEAK III CAMP PHOSPHODIESTERASE ACTIVITY

The test compounds are included in media comprising a radioactively labeled substrate $^3H$-cyclic nucleotide) such as adenosine 3':5'-monophosphate (cyclic AMP) and guanosine-3':5'-monophosphate (cyclic GMP), and a non-rate-limiting amount of 5'-nucleotidease isolated from a dog heart. The inhibition of the enzyme hydrolysis of the 5-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ionexchange resin or preferentially quenched with the ionexchange resin so that it is not quantitated with the liquid scintillation counter. Compounds of the present invention possess surprising and unexpected Peak III phosphodiesterase inhibiting activity.

The compounds of this invention can be normally adminstered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carrier or excipients. Suitable carriers include diluents or fillers, sterile aqueous media and various non-toxic organic solvents. The compositions may be formulated in the form of tablets, capsules. lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salt dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily. Some patients may respond quickly to a relatively large or small dose and require little or no maintenance dosage. On the other hand, other patients may require sustained dosing from about one to about four times a day depending on the physiological needs of the particular patient. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such patient should be effective to achieve and maintain the desired therapeutic response.

The following are exemplary preparations of compounds of the present invention.

EXAMPLE 1

METHYL-2-[4-(1H-IMIDAZOL-1-YL)BENZOYL]-BENZOATE

A solution of methyl-2-(4-fluorobenzoyl)benzoate (5.31 g, 21 mmol) in 23 mL of DMF is added dropwise to a solution of NaH (0.91 g, 23 mmol) and imidazole (1.43 g, 21 mmol) in 35 mL of DMF. The resulting mixture is heated at 120° C. for 20 hours under $N_2$. After cooling, the product is poured onto ice and extracted with $CHCl_3$ (4×30 mL). The combined extracts are dried ($Na_2SO_4$) and evaporated to give crude product. Chromatographic purification of the crude residue on silica gel (using EtOAc as the eluent) gives pure methyl-2-[4(1H-imidazol-1-yl)benzoyl]benzoate. M.P. 134.5°–136.5° C.

EXAMPLE 2

4-[4-(1H-IMIDAZOL-1-YL)PHENYL]-1-OXO-1,2-DIHYDROPHTHALAZINE

A solution of methyl-2-[4-(1H-imidazol-1-yl)benzoyl]benzoate (1.3 g, 4.25 mmol) in 15 mL of EtOH is treated with hydrazine monohydrate (0.26 g, 5.20 mmol) and heated to reflux for 1 day. The white solid which precipitates is filtered and recrystallized from EtOH to give 4[4-(1H-imidazol-1-yl)phenyl]-1-oxo-1,2-dihydrophthalazine. M.P. 309.5°–311° C.

EXAMPLE 3

3-(4-FLUOROBENZOYL)PYRIDINE-2-CARBOXYLIC ACID

A mixture of 2,3-pyridinedicarboxylic anhydride (9.0 g, 60.36 mmol) in 75 mL of fluorobenzene is warmed and stirred mechanically while $AlCl_3$ (17.7 g, 0.132 mol) is added portionwise from a powder addition funnel over 20 m. The resulting mixture is heated to reflux for 24 hours, then allowed to cool and the excess fluorobenzene decanted. Quenching of the residue with ice water and 5% aqueous HCl generates a solid which is filtered and washed with hot $H_2O$. The combined filtrates are evaporated to a final volume of ca. 250 mL, then heated to boiling and treated with a hot solution of 15% aqueous $CuSO_4$ solution to precipitate a blue solid. The suspension is filtered and the resulting solid resuspended in $H_2O$ (75 mL) and treated with a stream of $H_2S$ gas until the initial blue color of the suspension subsides and is replaced by a black suspension. The solid is filtered with the aid of Celite and the filtrate evaporated to produce a tan solid which is recrystallized from $H_2O$ to obtain 3-(4-fluorobenzoyl)pyridine-2-carboxylic acid. M.P. 153.5°–155° C.

EXAMPLE 4

3-(4-FLUOROBENZOYL)-2-CARBOMETHOXYPYRIDINE

Treatment of 3-(4-fluorobenzoyl)pyridine-2-carboxylic acid with diazomethane, followed by silica gel chromotography (using hexanes-EtOAc (3:2) as the eluent), gives pure 3-(4-fluorobenzoyl)-2-carbomethoxypyridine.

EXAMPLE 5

3-[4-(1H-IMIDAZOL-1-YL)BENZOYL]-2-CARBOMETHOXYPYRIDINE

A solution of 3-(4-fluorobenzoyl)-2-carbomethoxypyridine (2.37 g, 9.14 mmol) in 30 mL of DMF is added dropwise to a solution of NaH (0.43 g, 10.75 mmol) and imidazole (0.62 g, 9.14 mmol) in 26 mL of DMF. The mixture is heated at 120° C. for 1 day, then allowed to cool, quenched with ice $H_2O$, and extracted with EtOAc (3×50 mL). The combined organic layers are dried ($Na_2SO_4$), evaporated, and the residue chromatographed on silica gel (eluting with EtOAc-$CH_3OH$, 9:1) to generate 3-[4-(1H-imidazol-1-yl)benzoyl]-2-carbomethoxypyridine. M.P. 150°–157° C.

EXAMPLE 6

5-[4-(1H-IMIDAZOL-1-YL)PHENYL]-8-OXO-7,8-DIHYDROPYRIDO[2,3-d]PYRIDAZINE

A mixture of 3-[4-(1H-imidazol-1-yl)benzoyl]-2-carbomethoxypyridine (1.21 g, 3.94 mmol) in 50 mL of EtOH is treated with 0.22 g (4.33 mmol) of hydrazine monohydrate and heated to reflux for 1 day. The white solid which precipitates from the reaction mixture is filtered and recrystallized from DMF-$H_2O$ to give 5-[4-(1H-imidazol-1-yl)phenyl]-8-oxo-7,8-dihydropyrido[2,3-d]pyridazine. M.P. 359°–361° C.

EXAMPLE 7

7-(4-FLUOROPHENYL)-5-OXO-5,7-DIHYDROFURO[3,4-b]PYRIDINE

A suspension of 3-carbomethoxypicolinic acid (15.0 g, 0.083 mol) and 4-fluorobenzaldehyde (90.8 g. 0.732 mol) in 250 mL of p-cymene is heated to reflux under a stream of $N_2$ for 16 hours. The mixture is then allowed to cool to room temperature, filtered and the filtrate distilled in vacuo to remove p-cymene. A solution of the crude residue in $CH_2Cl_2$ is chromatographed on silica gel (using $Et_2O$-hexane (2:1) as the eluent). Recrystallization from hexane-EtOAc gives pure 7-(4-fluorophenyl)-5-oxo-5,7-dihydrofuro[3,4-b]pyridine. M.P. 116°–117.5° C.

EXAMPLE 8

3-CARBOMETHOXY-2-(4-FLUOROBENZOYL)-PYRIDINE

A suspension of 7-(4-fluorophenyl)-5-oxo-5,7-dihydrofuro[3,4-b]pyridine (2.93 g, 12.79 mmol) in 64 ml of 0.2N NaOH is heated to 75° C. with stirring for 24 hours. The mixture is then filtered and the filtrate evaporated to produce crude 2-pyridyl phenyl carbinol, which is not further purified, but rather, dissolved in 70 mL of pyridine and treated with chromium (VI) oxide pyridine complex (10.0 g, 38.78 mmol). A black mixture results which is stirred at 23° C. for 24 hours, then treated with saturated aqueous $NaHCO_3$ (50 ml) and extracted with $CHCl_3$ (3×75 mL). Acidification of the basic aqueous layer to pH 2 with concentrated HCl generates a precipitate which is filtered and dried to produce crude 2-(4-fluorobenzoyl)pyridine-3-carboxylic acid. Treatment of the latter with diazomethane in ether, followed by silica gel chromotography of the resulting solid (using hexane-EtOAc (3:1) as the eluent) produces 3-carbomethoxy-2-(4-fluorobenzoyl)pyridine. M.P. 95°–96.5° C.

EXAMPLE 9

2-[4-(1H-IMIDAZOL-1-YL)BENZOYL]-3-CARBOMETHOXYPYRIDINE

A solution of 3-carbomethoxy-2-(4-fluorobenzoyl)-pyridine (2.38 g, 9.18 mmol) in 7 ml of DMF is added dropwise to a mixture of NaH (0.25 g, 10.56 mmol) and imidazole (0.63 g, 9.18 mmol) in 25 mL of DMF. The mixture is heated at 120° C. for 20 hours, then allowed to cool, quenched with $H_2O$ and extracted with $CH_2Cl_2$ (4×50 mL). The combined organic layers are dried ($Na_2SO_4$) and evaporated to produce an oil. Chromatography on silica gel (using EtOAc-MeOH, 9.5:0.5 as the eluent) gives 2-[4-(1H-imidazol-1-yl)benzoyl]3-carbomethoxypyridine. M.P. 171°–173.5° C.

EXAMPLE 10

8-[4-(1H-IMIDAZOL-1-YL)PHENYL]-5-OXO-5,6-DIHYDROPYRIDO[3,2-d]PYRIDAZINE

A suspension of 2-[4-(1H-imidazol-1-yl)benzoyl]-3-carbomethoxypyridine (0.94 g, 3.06 mmol) in 50 mL of EtOH is treated with 0.36 g (7.17 mmol) of hydrazine monohydrate. The mixture is heated to reflux for 1 day, then allowed to cool and filtered to give crude product. Crystallization from DMF gives 8-[4-(1H-imidazol-1-yl)phenyl]-5-oxo-5,6-dihydropyrido[3,2-d]-pyridazine as white crystals. M.P. 376°–378° C.

EXAMPLE 11

3-(4-FLUOROBENZOYL)PYRIDINE-4-CARBOXYLIC ACID

AND

4-(4-FLUOROBENZOYL)PYRIDINE-3-CARBOXYLIC ACID

To a solution of pyridine-3,4-dicarboxylic anhydride (56.04 g, 0.38 mol) in 950 mL of fluorobenzene is added $AlCl_3$ (126.67 g, 0.95 mol) over 45 min. from a powder addition funnel. The mixture is heated to reflux for 12 hours, then allowed to cool and quenched with ice water. Addition of a concentrated NaOH solution results in a solid precipitate which is filtered. The basic aqueous fraction of the biphasic filtrate is separated, washed with $Et_2O$ (3×150 mL), and acidified to pH 2.5 with concentrated HCl to generate a white solid which is collected by vacuum filtration. The solid is washed with several portions of hot MeOH to generate pure 3-(4-fluorobenzoyl)pyridine-4-carboxylic acid. M.P. 308.5° C. The combined methanolic filtrates are evaporated and recrystallized from MeOH to generate 4-(4-fluorobenzoyl)-pyridine-3-carboxylic acid. M.P. 231°–232.5° C.

EXAMPLE 12

3-(4-FLUOROBENZOYL)PYRIDINE-4-CARBOXYLIC ACID

A mixture of 4-carbomethoxynicotinic acid (2.0 g, 11.04 mmol) in 20 mL of SOCl₂ is heated to reflux for 4 hours, then allowed to cool. Evaporation of excess SOCl₂ results in 4-carbomethoxynicotinoyl chloride HCl which is suspended in fluorobenzene (15 ml) and treated with AlCl₃ (4.04 g, 30.3 mmol). After heating at reflux for 2 hours, the reaction is quenched with ice and neutralized with aqueous NaOH to generate a precipitate which is filtered. The aqueous fraction of the biphasic filtrate is separated, washed with several portions of EtOAc and acidified to pH 3.5 with 5% aqueous HCl to generate a white solid. The solid is collected by filtration, washed with H₂O, and dried by suction to generate 3-(4-fluorobenzoyl)pyridine-4-carboxylic acid.

EXAMPLE 13

3-[4-(1H-IMIDAZOL-1-YL)BENZOYL]-4-CARBOMETHOXYPYRIDINE

A solution of 3-(4-fluorobenzoyl)-4-carbomethoxypyridine (2.25 g, 8.68 mmol) in 10 mL of DMF is added dropwise to a solution of NaH (0.25 g, 10.21 mmol) and imidazole (0.59 g, 8.68 mmol) in 26 mL of DMF. The mixture, after heating at 120° C. for 1 day, is allowed to cool, quenched with ice water, and extracted with EtOAc (3×75 mL). The combined organic layers are dried (Na₂SO₄) and evaporated to produce crude product. Chromatographic purification on silica gel (using EtOAc-MeOH, 9:1 as the eluent) gives pure 3-[4-(1H-imidazol-1-yl)benzoyl]-4-carbomethoxypyridine as a light brown solid. M.P. 125°–128° C.

EXAMPLE 14

4-[4-(1H-IMIDAZOL-1-YL)BENZOYL]-3-CARBOMETHOXYPYRIDINE

A solution of 4-(4-fluorobenzoyl)-3-carbomethoxypyridine (2.05 g, 7.91 mmol) in 20 mL of DMF is added dropwise to NaH (0.37 g, 9.10 mmol) and imidazole (0.54 g, 7.91 mmol) in 35 mL of DMF. Using the same reaction conditions and workup as those used in Example 13, leads to the recovery of crude product. Chromatographic purification on silica gel (using EtOAc-MeOH, 95:5 as the eluent) gives pure 4-[4-(1H-imidazol-1-yl)benzoyl]-3-carbomethoxypyridine. M.P. 135°–137° C.

EXAMPLE 15

4-[4-(1H-IMIDAZOL-1-YL)PHENYL]-1-OXO-1,2-DIHYDROPYRIDO[3,4-d]PYRIDAZINE

A solution of 0.43 g (1.4 mmol) of 3-[4-(1H-imidazol-1-yl)benzoyl]-4-carbomethoxypyridine in 50 mL of EtOH is treated with hydrazine monohydrate (0.08 g, 1.54 mmol) and heated to reflux for 1 day. The mixture is allowed to cool and the white solid precipitate filtered and dried to produce 4-[4-(1H-imidazol-1-yl)phenyl]-1-oxo-1,2-dihydropyrido[3,4-d]pyridazine. M.P. 377° C. dec.

EXAMPLE 16

4-[4-(1H-IMIDAZOL-1-YL)PHENYL]-1-OXO-1,2-DIHYDROPYRIDO[4,3-d]PYRIDAZINE

Treatment of a solution of 0.55 g (1.79 mmol) of 4-[4-(1H-imidazol-1-yl)benzoyl]-3-carbomethoxypyridine and hydrazine monohydrate (0.11 g, 2.15 mmol) in 50 mL of EtOH at reflux for 1 day generates 4-[4-(1H-imidazol-1-yl)phenyl]-1-oxo-1,2-dihydropyrido[4,3-d]pyridazine. M.P. >250° C.

EXAMPLE 17

When imidazole is replaced in the above examples by 1,2,4-triazole then the corresponding 1,2,4-triazol-1-yl product is prepared.

EXAMPLE 18

When hydrazine of the foregoing examples is replaced by a substituted hydrazine of the table below then the corresponding product is obtained.

| | |
|---|---|
| NH₂NHCH₃ | NH₂NHCONH₂ |
| NH₂NHCH₂CH₃ | NH₂NHC(=NH)NH₂ |
| NH₂NHCH₂Ph | NH₂NHCONHSO₂—p-tolyl |
| NH₂NH(CH₂)₂Ph | NH₂NHSO₂—p-tolyl |
| NH₂NHCOCH₃ | |
| NH₂NHCH₂CH₂OH | |
| NH₂NHCH₂CO₂CH₂CH₃ | |

We claim:

1. A compound of formula:

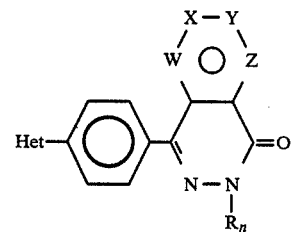

wherein:

Het is imidazol-1-yl or 1,2,4-triazol-1-yl;

W, X, Y and Z are C or not more than one is a N atom;

R_n is hydrogen,
 alkyl,
 benzyl,
 phenethyl,
 acetyl,
 propionyl,
 benzoyl,
 carbalkoxy,
 carbamyl,
 carbalkoxyalkyl,
 hydroxyalkyl,
 alkoxyalkyl or
 amidino;

where alkyl has 1 to 6 carbon atoms and alkoxy has 1 to 4 carbon atoms; or a pharmaceutically acceptable salt thereof.

2. A compound according to claim 1 which is

3. A compound according to claim 1 which is

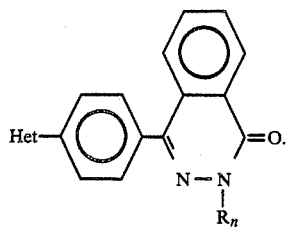

4. A compound according to claim 1 which is

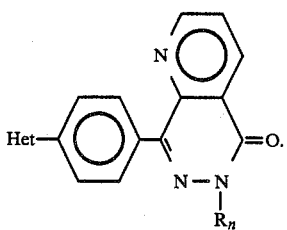

5. A compound according to claim 1 which is

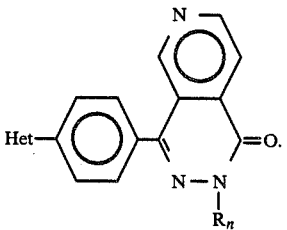

6. A compound according to claim 1 which is

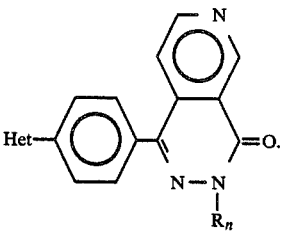

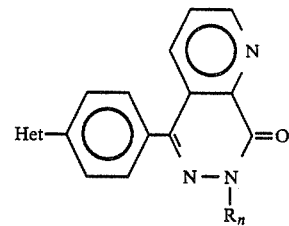

7. A compound according to claim 2 where Het is 1H-imidazol-1-yl and $R_n$ in hydrogen.
8. A compound according to claim 3 where Het is 1H-imidazol-1-yl and $R_n$ in hydrogen.
9. A compound according to claim 4 where Het is 1H-imidazol-1-yl and $R_n$ in hydrogen.
10. A compound according to claim 5 where Het is 1H-imidazol-1-yl and $R_n$ in hydrogen.
11. A compound according to claim 6 where Het is 1H-imidazol-1-yl and $R_n$ in hydrogen.
12. A method for increasing cardiotonic contractility in a human or other mammal requiring such treatment which comprises administering thereto an effective inotropic amount of compound of the formula:

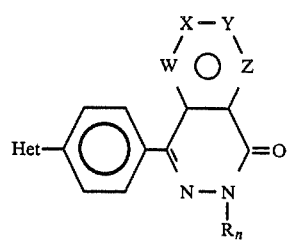

wherein:
Het is imidazol-1-yl or 1,2,4-triazol-1-yl;
W, X, Y and Z are C or not more than one is a N atom;
$R_n$ is hydrogen,
  alkyl,
  benzyl,
  phenethyl,
  acetyl,
  propionyl,
  benzoyl,
  carbalkoxy,
  carbamyl,
  carbalkoxyalkyl,
  hydroxyalkyl,
  alkoxyalkyl or
  amidino;
where alkyl has 1 to 6 carbon atoms and alkoxy has 1 to 4 carbon atoms; or
pharmaceutically acceptable salt thereof.
13. A pharmaceutical composition comprising an effective cardiotonic amount of a compound according to claim 1 in admixture with a pharmaceutically acceptable carrier.

* * * * *